United States Patent
Aufrichtig et al.

(10) Patent No.: US 6,521,886 B2
(45) Date of Patent: Feb. 18, 2003

(54) METHOD OF MONITORING CHANGES IN THE DETECTIVE QUANTUM EFFICIENCY OF AN X-RAY DETECTOR

(75) Inventors: Richard Aufrichtig, Mountain View, CA (US); Paul R. Granfors, Sunnyvale, CA (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 42 days.

(21) Appl. No.: 09/751,978

(22) Filed: Dec. 29, 2000

(65) Prior Publication Data

US 2002/0117613 A1 Aug. 29, 2002

(51) Int. Cl.⁷ .............................................. G12B 13/00
(52) U.S. Cl. ................... 250/252.1; 250/483.1
(58) Field of Search .................... 250/252.1, 483.1, 250/208.1; 430/496, 403, 502, 966; 378/207

(56) References Cited

U.S. PATENT DOCUMENTS

| | | | |
|---|---|---|---|
| 4,996,413 A | | 2/1991 | McDaniel et al. |
| 5,021,327 A | * | 6/1991 | Bunch et al. ................ 430/496 |
| 5,841,835 A | | 11/1998 | Aufrichtig et al. |

* cited by examiner

Primary Examiner—Constantine Hannaher
Assistant Examiner—Otilia Gabor
(74) Attorney, Agent, or Firm—Peter Vogel

(57) ABSTRACT

Automated measurement of changes in detective quantum efficiency (DQE) within an x-ray detector. The calculation of relative DQE changes is limited to the measurement of two quantities, namely MTF(f) and NPS(f). The measurement of MTF is obtained using an image quality phantom technique. The measurement of NPS includes the use of a flat field phantom, and data can be obtained during system calibration. Detector degradation and potential field replacement, are determined by monitoring the ratio of DQE as a function of time.

20 Claims, 1 Drawing Sheet

Figure 1:
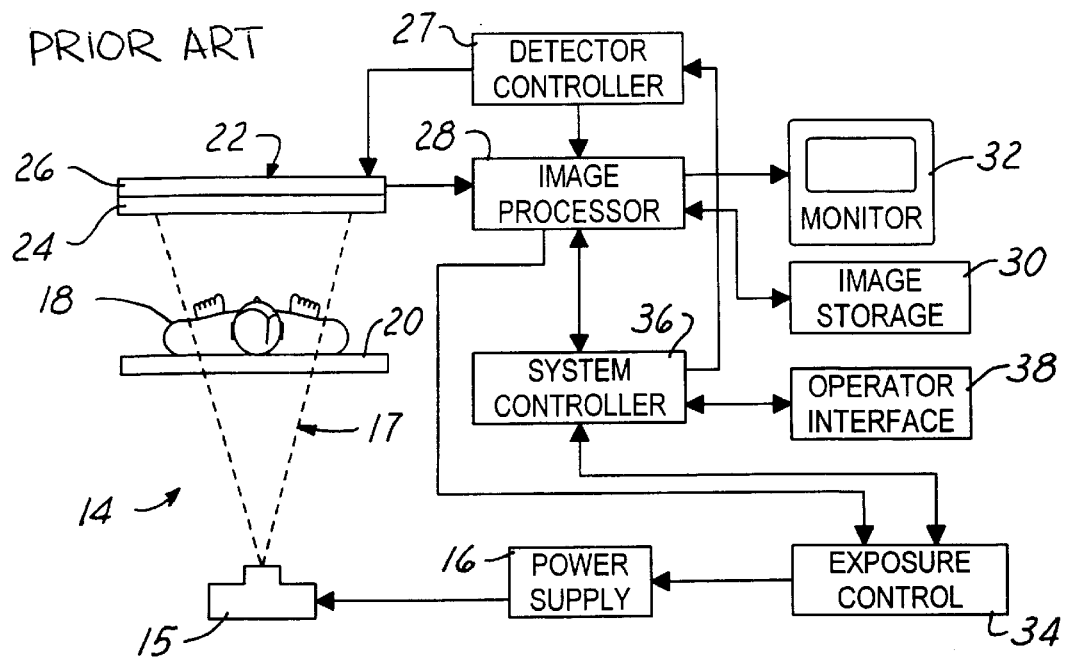

METHOD OF MONITORING CHANGES IN THE DETECTIVE QUANTUM EFFICIENCY OF AN X-RAY DETECTOR

TECHNICAL FIELD

The present invention relates to x-ray detectors and more particularly to methods for monitoring changes in the detective quantum efficiency of x-ray detectors.

BACKGROUND OF THE INVENTION

X-ray systems have been used for some time for imaging and measuring objects, such as medical patients. X-ray beams projected from a source pass through the object or patient and are detected by an x-ray detector and then converted into a visible light image. High resolution solid state x-ray detectors are currently in use and are beneficial to the analysis of the patient. The digital x-ray detectors typically utilize two-dimensional arrays of photodiode detector elements which produce electrical signals corresponding to the brightness of a picture element in the x-ray image projected onto it. The signals from the detector elements are read out individually and digitized for further imaging processing, storage and display.

In order to insure consistent and accurate measurements from the x-ray detectors, it is necessary to periodically monitor the detectors in order to evaluate potential detector degradations. X-ray imaging detectors may change over time and it is necessary to measure and track changes in the detectors for maintenance and/or replacement when necessary. The detective quantum efficiency (DQE) is recognized as one of the important objective measures of the performance of an x-ray imaging detector. DQE is the measure of the ability of the detector to transfer signal-to-noise ratio from its input to its output. Currently, the ability to measure or calculate the quantities and factors necessary for a determination of DQE is complicated and time-consuming. Typically, measurements of DQE can only be satisfactorily performed by trained and skilled physicists.

There thus is a need for an easier and less complicated methodology or system for measuring or tracking changes in the detective quantum efficiency of an x-ray imaging detector.

SUMMARY OF THE INVENTION

The present invention provides an improved methodology for determining changes in the detective quantum efficiency of an x-ray imaging detector. The present invention also automatically measure changes in detective quantum efficiency within an x-ray detector without relying upon complicated sets of measurements.

With the present invention, a mathematical equation and relationship has been developed which meets the above-stated objectives and overcomes the problems currently existing with present DQE measurements. With the invention, the calculation of relative DQE changes is limited to the calculation and measurement of only two quantities, both of which can be achieved in an automatic fashion on a digital x-ray system. One of the quantities, namely the modulation transfer function (MTF), is obtained using an edge phantom made from a piece of x-ray absorbing material, or a linepair bar pattern that is positioned in front of the image detector. The measurement of the second quantity, namely the noise power spectrum (NPS), is secured from the use of flat field images and may be calculated from data obtained during system calibration.

The possible degradation of the detector and the potential need for field replacement can be determined by monitoring a DQE ratio as a function of time. This DQE ratio is obtained from ratios of MTF and normalized NPS. A computer stores the MTF and NPS quantities when they are measured at system calibration and over time. When the MTF and NPS data are acquired, the computer then directly calculates the DQE change at certain frequencies. If the DQE falls below a specification limit, a warning is displayed to the operator or field engineer.

Other objects, benefits, and features of the present invention will become apparent after review and analysis of the following description of the invention, when taken in accordance with the attached drawings and appended claims.

BRIEF DESCRIPTION THE DRAWINGS

Figure 2:
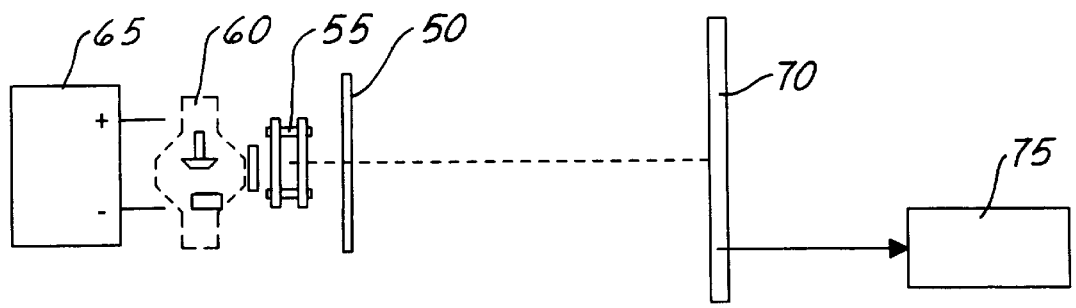

FIG. 1 is a schematic diagram of an x-ray imaging system in which the present invention can be utilized; and FIG. 2 is a schematic diagram of a system for measuring one of the quantities, the NPS, needed for the present invention.

DESCRIPTION OF THE PREFERRED EMBODIMENT(S)

FIG. 1 schematically illustrates a representative x-ray system in which the present invention can be utilized. With reference to FIG. 1, an x-ray apparatus 14 includes an x-ray tube 15, which, when excited by a power supply 16, emits an x-ray beam 17. As illustrated, the x-ray beam is directed toward a patient lying on an x-ray transmissive table 20. A portion of the beam which is transmitted to the table and the patient impinges upon an x-ray detector designated 22. The invention can be utilized with any detector, such as, for example the type of detector 22 which includes an x-ray imager 24 and cooling mechanism 26.

The x-ray detector comprises a solid state image sensor formed by a two-dimensional array of photo detectors arranged in columns and rows. Several thousand photo detectors are positioned in each column and row connected to a common output line. A scintillator absorbs x-ray photons and converts them to light. Low noise photodiode array absorbs light and converts it into an electronic charge. Each photodiode represents a pixel or picture element. The electrical charge at each pixel is read out by low-noise electronics and turned into digital data sent to an image processor 28. The image processor includes circuitry for processing and enhancing the x-ray image signal. The processed image is then typically displayed on a video monitor 32 and may be archived in an image storage device 30. The overall operation of the x-ray apparatus 14 is governed by a system controller 36 which receives commands from the x-ray technician through an operator interface panel 38.

One of the problems with x-ray detectors is that their imaging characteristics may change over time. It thus is necessary to constantly or periodically monitor the performance of the x-ray detectors for maintenance or replacement, or in order to make other adjustments to compensate for such changes.

One of the important objective measures of the performance of an x-ray imaging detector is the "detective quantum efficiency," also known as the "DQE". The DQE is a measure of the ability of the x-ray detector to transfer signal-to-noise ratio from its input to its output. This is an important parameter to track as a function of time to evaluate potential detector degradations.

The DQE is a function of spatial frequency "f" and be computed by the following equation:

$$DQE(f) = \frac{(S \cdot MTF(f))^2}{NPS(f) \cdot X \cdot C} \qquad (1)$$

As can be seen from Equation (1), five quantities must be measured or calculated to obtain DQE(f). In this regard, S is the average signal, MTF is the modulation transfer function, NPS is the noise power spectrum, X is the x-ray exposure, and C is the x-ray fluence per exposure.

Methods for obtaining each of these five quantities in Equation (1) have been described in the literature and are well known. It is not believed necessary to describe each of them here.

On x-ray systems installed in the field, the procedure for obtaining the five quantities in order to determine DQE in accordance with Equation (1) includes a complicated set of measurements. In particular, the x-ray exposure must be carefully measured. It is possible that the MTF and NPS may change over time and potentially reduce the DQE. Also, on an x-ray system, it is difficult to accurately measure the entrance exposure X in order to accurately compute the DQE. In practice, only skilled physicists are capable of performing the DQE measurement as set forth in Equation (1).

With the present invention, a new test methodology for determining relative changes in DQE(f) is provided. The invention monitors relative changes in DQE without requiring any particular operator skills. For the calculation of DQE(f) in accordance with the present invention, it is not necessary to measure or ascertain all of the five quantities of Equation (1).

In accordance with the methodology of the present invention, the following analysis is made. First, DQE at zero frequency, namely DQE(0) can be shown to be independent of the x-ray exposure at high x-ray exposure, and to be directly proportional to the absorption of the x-ray detector. Also, DQE(0) equals $A_S*N$ where N is the detector dependent x-ray absorption which is a constant and $A_s$ is a statistical factor which empirically has been found to be substantially constant for a particular detector.

In general, DQE(f) can be written as follows:

$$DQE(f)=k* MTF^2(f)/NPS(f) \qquad (2)$$

A constant "k" is a proportionality constant that is defined by the following equation:

$$k=DQE(0)*NPS(0) \qquad (3)$$

Based on the above equations, the ratio of two DQE measurements can be written as follows:

$$\frac{DQE_1(f)}{DQE_2(f)} = \frac{DQE_1(0) \cdot \frac{(MTF_1(f))^2}{NPS_1(f)/(NPS_1(0)}}{DQE_2(0) \cdot \frac{(MTF_2(f))^2}{NPS_2(f)/NPS_2(0)}} \qquad (4)$$

$$= \frac{(MTF_1(f))^2}{(MTF_2(f))^2} \cdot \frac{NPS_2(0)}{NPS_2(0)} \cdot \frac{NPS_2(f)}{NPS_1(f)}$$

$$= \frac{(MTF_1(f))^2}{(MTF_2(f))^2} \cdot \frac{NNPS_2(f)}{NNPS_1(f)}$$

where NNPS(f), the normalized noise power spectrum, is equal to NPS(f)/NPS(0). In Equation (4), the following is assumed:

$$DQE_1(0)=DQE_2(0)=DQE(0) \qquad (5)$$

Equation (5) holds true for a sufficiently large exposure. The subscripts "1" and "2" indicate two different measurements, for example at two different time instances.

Based on the above relationships, the calculation of relative DQE changes is limited to the measurement of only two quantities, namely MTF(f) and NNPS(f). Each of these two quantities can be achieved in an automatic fashion on a digital x-ray system.

The measurement of MTF is obtained using an edge phantom made from a thin piece of x-ray absorbing material (tungsten), or a linepair bar pattern that is positioned in front of the image detector. A representative image quality test phantom device is shown and described, for example, in U.S. Pat. No. 5,841,835, the disclosure which is hereby incorporated by reference herein. This patent gives an example of the hardware and software needed for the MTF measurement.

The measurement of the NPS quantity requires the use of flat field images. A representative setup for such measurements is shown in FIG. 2. A uniform x-ray absorbing filter 50, such as a 2 cm thick block of aluminum, is positioned in front of a collimator 55, and images are acquired with the image detector 70 and transferred to a computer 75. An x-ray tube 60 operated by high voltage generator 65 provides a necessary x-ray beam. The flat field image provided by the flat field phantom is the type typically required during a regular detector calibration. At the time that the standard calibration is being performed, the NPS could be calculated from the same images.

The accurate estimation of NPS(f) at low frequencies and in particular at zero frequency, namely NPS(0), may require a large number of images. However, it has been shown that NPS (0.5 cycles/mm.) can be reliably measured with as few as ten flat field images frames. Since MTF(0)=1 by definition, and since generally MTF(f) does not degrade with time at a low frequency such as 0.5 cycles/mm., NNPS(f) in equation (4) can be approximated by $$NNPS(f) \approx \frac{NPS(f)}{NPS(0.5)},$$

and
equation (4) then can be modified to the following:

$$\frac{DQE_1(f)}{DQE_2(f)} \approx \frac{(MTF_1(f))^2}{(MTF_2(f))^2} \cdot \frac{NPS_1(0.5)}{NPS_2(0.5)} \cdot \frac{NPS_2(f)}{NPS_1(f)} \text{ for} \qquad (6)$$

$$f \geq 0.5 \text{ cycles/mm}$$

To reduce any uncertainty in the NPS(0.5) measurement, curve fitting of the entire dataset may be used prior to an NPS(0.5) estimation, which minimizes the measurement noise. An alternate method of obtaining NNPS(f) is to divide NPS(f) by the average signal in the flat field images used to obtain NPS(f). Detector degradation and potential field replacement can be determined by monitoring the ratio set forth in Equation (6) as a function of time. That requires the computer 75 in FIG. 2 to store the $MTF_1(f)$ and $NNPS_1(f)$ functions when they are measured at initial system installation. For measurements of $MTF_2(f)$ and $NNPS_2(f)$ over time, the computer 75 can directly calculate the DQE change at frequencies such as 1.0, 1.5, 2.0, 2.5, or higher cycles/mm.

Preferably, the x-ray system has a warning light or bell of some type in order to display a warning of out-of-normal situations to the operator or field engineer. In this manner, if the DQE falls below the specification limit, a warning can be generated and displayed to the operator or engineer indicating that maintenance and/or replacement of the x-ray detector may be required.

The present invention provides a process to measure and track relative changes in DQE without requiring any non-standard x-ray measurements. Changes in DQE are obtained directly by approximately normalizing measured MTF and NPS functions. X-ray exposure measurements are not required.

Another use of the DQE data is to produce trending charts which may be accessed remotely and used to monitor the performance of the detector.

While the invention has been described in connection with one or more embodiments, it is to be understood that the specific mechanisms and techniques which have been described are merely illustrative of the principles of the invention. Numerous modifications may be made to the methods and apparatus described without departing from the spirit and scope of the invention as defined by the appended claims.

What is claimed is:

1. A process for determining changes in detective quantum efficiency (DQE) of an x-ray detector in an x-ray system comprising:

determining a modulation transfer function (MTF) of the x-ray detector using an image quality phantom;

determining a noise power spectrum (NPS) of the x-ray detector using flat field images;

calculating a normalized noise power spectrum (NNPS);

computing a ratio of $(MTF)^2/NNPS$; and monitoring said ratio as a function of time.

2. The process as set forth in claim 1 wherein the step of calculating the NNPS is carried out during calibration of the x-ray system.

3. The process as set forth in claim 1 wherein the x-ray detector acquires images and wherein the x-ray system has a collimator and computer and the step of determining the NPS is carried out by positioning a uniform x-ray absorbing filter in front of the collimator and transferring said images acquired by the x-ray detector to the computer where the NPS is determined.

4. The process as set forth in claim 1 wherein an edge phantom is positioned in front of the x-ray detector when the MTF is determined.

5. The process as set forth in claim 1 wherein a linepair bar pattern is positioned in front of the x-ray detector when the MTF is determined.

6. The process as set forth in claim 1 wherein the change in DQE is determined at frequencies greater than or equal to 0.5 cycles/mm.

7. The process as set forth in claim 6 further comprising the step of curve fitting a data set prior to the NPS determination, wherein measurement noise is minimized.

8. The process as set forth in claim 1 further comprising the step of minimizing measurement noise.

9. The process as set forth in claim 8 wherein measurement noise is minimized by curve fitting a data set prior to the NPS determination at frequencies at least as great as 0.5 cycles/mm.

10. The process as set forth in claim 1 wherein said monitoring is carried out by the following:

$$\frac{DQE_1(f)}{DQE_2(f)} \approx \frac{(MTF_1(f))^2}{(MTF_2(f))^2} \cdot \frac{NNPS_2(f)}{NNPS_1(f)}$$

wherein $DQE_1(f)$ and $DQE_2(f)$ are measurements of the detective quantum efficiency at two different points in time, $MTE_1(f)$ and $MTE_2(f)$ are measurements of the modulation transfer function at said two points in time, and $NNPS_1$ and $NNPS_2$ are measurements of the normalized noise power spectrum at said two points in time.

11. The process as set forth in claim 10 wherein NNPS (f)=NPS(f)/NPS(0).

12. The process as set forth in claim 10 wherein NNPS (f)=NPS(f)/NPS(0.5).

13. The process as set forth in claim 10 wherein NNPS(f) is determined by dividing NPS(f) by an average signal in the flat field images used to obtain NPS(f).

14. The process as set forth in claim 1 wherein said ratio is monitored as a function of time by a computer.

15. The process as set forth in claim 14 wherein a first reading of MTF and NPS take place at initial system install.

16. The process as set forth in claim 1 further comprising the step of displaying a warning if the DQE falls below a prespecified limit.

17. The process as set forth in claim 1 wherein the x-ray detector is a digital x-ray detector.

18. The process as set forth in claim 1 wherein the DQE data generated by monitoring the ratio as a function of time is used for trending analysis.

19. The process as set forth in claim 1 further comprising the step of producing trending charts with the DQE data generated by monitoring the ratio as a function of time.

20. The process as set forth in claim 1 further comprising the step of remotely accessing the DQE data generated by monitoring the ratio as a function of time.

* * * * *